US007326402B2

(12) United States Patent
Recipon et al.

(10) Patent No.: US 7,326,402 B2
(45) Date of Patent: Feb. 5, 2008

(54) METHOD OF DIAGNOSING, MONITORING, STAGING, IMAGING AND TREATING CANCER

(75) Inventors: Herve Recipon, San Francisco, CA (US); Roberto A. Macina, San Jose, CA (US); Sei-Yu Chen, Foster City, CA (US); Yongming Sun, San Jose, CA (US)

(73) Assignee: diaDexus, Inc., South San Francisco, CA (US)

( * ) Notice: Subject to any disclaimer, the term of this patent is extended or adjusted under 35 U.S.C. 154(b) by 371 days.

(21) Appl. No.: 11/068,678

(22) Filed: Feb. 28, 2005

(65) Prior Publication Data
US 2005/0152837 A1 Jul. 14, 2005

Related U.S. Application Data

(62) Division of application No. 09/705,500, filed on Nov. 3, 2000, now Pat. No. 6,902,890.

(60) Provisional application No. 60/163,444, filed on Nov. 4, 1999.

(51) Int. Cl.
*C12Q 1/00* (2006.01)
*G01N 33/53* (2006.01)
*A61K 51/10* (2006.01)
*A61B 5/055* (2006.01)

(52) U.S. Cl. .................... 424/1.49; 424/9.3; 435/4; 435/7.1; 435/7.8

(58) Field of Classification Search ............... None
See application file for complete search history.

(56) References Cited

U.S. PATENT DOCUMENTS

| 4,846,187 | A | * | 7/1989 | Siegel ................. 600/436 |
| 5,747,264 | A | | 5/1998 | Schmidt et al. ............. 435/7.1 |
| 5,837,498 | A | | 11/1998 | Olsen et al. ............. 435/69.4 |
| 5,877,290 | A | | 3/1999 | Olsen et al. ............. 530/387 |
| 5,994,103 | A | | 11/1999 | Olsen et al. |
| 5,994,301 | A | | 11/1999 | Olsen et al. |
| 6,027,887 | A | | 2/2000 | Zavada et al. |

FOREIGN PATENT DOCUMENTS

| EP | 1033401 A2 | 9/2000 |
| EP | 1121936 A1 | 8/2001 |
| JP | 0229880 A2 | 8/2000 |
| WO | WO 95/24411 A1 | 9/1995 |
| WO | WO 95/34650 A2 | 12/1995 |
| WO | WO 96/13610 A2 | 5/1996 |
| WO | WO 98/20165 A2 | 5/1998 |
| WO | WO 98/24914 A1 | 6/1998 |
| WO | WO 98/45436 A2 | 10/1998 |
| WO | WO 00/09657 A2 | 2/2000 |
| WO | WO 00/16795 A1 | 3/2000 |
| WO | WO 00/24913 A2 | 5/2000 |
| WO | WO 00/55174 A1 | 9/2000 |
| WO | WO 00/57903 A2 | 10/2000 |
| WO | WO 01/00828 A2 | 1/2001 |
| WO | WO 01/05422 A2 | 1/2001 |
| WO | WO 01/05828 A1 | 1/2001 |
| WO | WO 01/14550 A1 | 3/2001 |
| WO | WO 01/23541 A2 | 4/2001 |
| WO | WO 01/30969 A2 | 5/2001 |
| WO | WO 01/32209 A1 | 5/2001 |

OTHER PUBLICATIONS

Antoinia et al (International Immunology, 1995, vol. 7, pp. 715-725).*
Abstract of Algarra et al International Journal of Clinical and Laboratory Research, 1997, vol. 27, pp. 95-102).*
Bodey et al (Anticancer Research, Jul.-Aug. 2000, vol. 20, pp. 2665-2676).*
Ohlen et al (Journal of Immunology, 2001, vol. 166, pp. 2863-2870).*
Abstract of Semino et al (Journal of Biological Regulators and Homeostatic Agents, 1993, vol. 7, pp. 99-105.*
Tolcher et al (Clinical Cancer Research, 2002, vol. 8, pp. 2530-2535).*
Cripps et al (Clinical Cancer Research. 2002, 8, pp. 2188-2192).*
Marshall et al (Clinical Colorectal Cancer, 2004, vol. 4, pp. 268-274).*
Oza et al (Gynecological Oncology, 2003, vol. 89, pp. 129-133).*
Paul, Fundamental Immunology, (text), 1993, pp. 1157-1170.*
Apostolopoulos et al (Nature Medicine, 1998, vol. 4, pp. 315-320).*
Jager et al (PNAS, 2000, vol. 97, pp. 12198-12203).*
Stedman's Medical dictionary, 2000, Vaccine Definition, lines 1-3.*
Abstract of Wheeler (Salud p'ublica de M'exico, (Jul.-Aug. 1997) 39 (4) 283-7).*
Efferson et al (Anticancer Research, 2005, vol. 25, pp. 715-724).*
Bachman et al (Journal of Immunology, 2005, vol. 175, pp. 4677-4685).*
Yu and Restifo (Journal of Clinical Investigation, 2002, vol. 110, pp. 289-294.*
Charpentier et al., "STC2 and E2IG1, Two Novel Breast Cancer Biomarkers", Proceedings of the American Association for Cancer Research Annual 2001 42:628 XP001119829.
Chen et al., "Evidences of human stanniocalcin 1 and amino acid transporter ATBO+ as potential diagnostic marker for non-small cell lung cancer", American Association for Cancer Research Annual 2002 43:518-519 XP001119830.
Kahn et al., "Gene Expression Profiling in an in Vitro Model of Angiogenesis", American Journal of Pathology 2000 156 (6) :1887-1900 XP-002178225.
Liang et al., "Differential Display and Cloning of Messenger RNAs from Human Breast Cancer versus Mammary Epithelial Cells[1]", Cancer Research 1992 52:6966-6968 XP002032010.

(Continued)

*Primary Examiner*—Karen A. Canella
(74) *Attorney, Agent, or Firm*—Licata & Tyrrell P.C.; Keith R. McCollum

(57) ABSTRACT

The present invention provides new methods for detecting, diagnosing, monitoring, staging, prognosticating, imaging and treating cancer.

17 Claims, No Drawings

OTHER PUBLICATIONS

Chang et al., A novel human cDNA highly homologous to the fish hormone stannioicalcin. Mol Cell Endocrinol. 1995; vol. 112:241-247.

Change et al., Human Stanniocalcin (STC): Genomic Structure, Chromosomal Localization, and the Presence of CAG Trinucleotide Repeats, Genomics, 1998; vol. 47:393-398.

De Niu et al., Immunolocalization of stanniocalcin in human kidney. Mol Cell Endocrinol. Feb. 1998; vol. 137(2):155-9.

Ellis et al., Post-transcriptional Regulation of the Stanniocalcin Gene by Calcium. JBC. Jan. 27, 1995;vol. 270(4):1960-65.

Fujiwara et al., Assessment of Stanniocalcin-1 mRNA as a molecular marker for micrometastases of various human cancers. Int. J. Oncol. Apr. 2000;vol. 16:799-804.

Haddad et al., Immunocytochemical Localization of Stannniocalcin Cells in the Rat Kidney. Endocrinology. 1996;vol. 137(5):2113-17.

Olsen et al., Human stanniocalcin: A possible hormonal regulator of mineral metabolism. Biochemistry. 1996;vol. 93:1792-96.

Varghese et al., Comparative Analysis of Mammalian Stanniocalcin Genes. Endocrinology. 1998;vol. 139(11):4714-25.

Verbost et al., Studies on stanniocalcin: characterization of bioactive and antigenic domains of the hormone. Mol Cell Endocrinol. 1993;vol. 93:11-16.

Wagner et al., Immunological and biological evidence for a stanniocalcin-like hormone in human kidney. Physiology. Mar. 1995;vol. 92:1871-75.

* cited by examiner

SEQUENCE LISTING

<160> NUMBER OF SEQ ID NOS: 5

<210> SEQ ID NO 1
<211> LENGTH: 503
<212> TYPE: DNA
<213> ORGANISM: Homo sapiens

<400> SEQUENCE: 1

```
ctatatatgt atctacaata catatatcta cacatacaga aagaagcagt tctcacaatg      60
ttgctagttt tttgcttctc tttcccccac cctactccct ccaattcccc cttaaacttc     120
caaagcttcg tcttgtgttt gctgcagagt gattcggggg ctgacctaga ccagtttgca     180
```

| | |
|---|---:|
| tgattcttct cttgtgatttt ggttgcactt tagacatttt tgtgccatta tatttgcatt | 240 |
| atgtatttat aatttaaatg atatttaggt ttttggctga gtactggaat aaacagtgag | 300 |
| catatctggt atatgtcatt atttattgtt aaattacatt tttaagctcc atgtgcatat | 360 |
| aaaggttatg aaacatatca tggtaatgac agatgcaagt tattttattt gcttattttt | 420 |
| ataattaaag atgccatagc ataatatgaa gcctttggtg aattccttct aagataaaaa | 480 |
| taataataaa gtgttacgtt tta | 503 |

```
<210> SEQ ID NO 2
<211> LENGTH: 3762
<212> TYPE: DNA
<213> ORGANISM: Homo sapiens
<220> FEATURE:
<221> NAME/KEY: unsure
<222> LOCATION: (2370)..(2405)
<220> FEATURE:
<221> NAME/KEY: unsure
<222> LOCATION: (2456)
<220> FEATURE:
<221> NAME/KEY: unsure
<222> LOCATION: (2795)..(2824)
<220> FEATURE:
<221> NAME/KEY: unsure
<222> LOCATION: (3177)
<220> FEATURE:
<221> NAME/KEY: unsure
<222> LOCATION: (3181)
<220> FEATURE:
<221> NAME/KEY: unsure
<222> LOCATION: (3184)
<220> FEATURE:
<221> NAME/KEY: unsure
<222> LOCATION: (3191)
```

<400> SEQUENCE: 2

| | |
|---|---:|
| ggtggcagca gcagcatcac acgtaacaac aacaaaaaaa aatcctcatc aaatcctcac | 60 |
| ctaagctttc agtgtatcca gatccacatc ttcactcaag ccaggagagg gaaagaggaa | 120 |
| agggggggcag gaaaaaaaaa aaacccaaca acttagcgga aacttctcag agaatgctcc | 180 |
| aaaactcagc agtgcttctg gtgctggtga tcagtgcttc tgcaacccat gaggcggagc | 240 |
| agaatgactc tgtgagcccc aggaaatccc gagtggcggc tcaaaactca gctgaagtgg | 300 |
| ttcgttgcct caacagtgct ctacaggtcg gctgcgggc ttttgcatgc ctggaaaact | 360 |
| ccacctgtga cacagatggg atgtatgaca tctgtaaatc cttcttgtac agcgctgcta | 420 |
| aatttgacac tcagggaaaa gcattcgtca agagagctt aaaatgcatc gccaacgggg | 480 |
| tcacctccaa ggtcttcctc gccattcgga ggtgctccac tttccaaagg atgattgctg | 540 |
| aggtgcagga agagtgctac agcaagctga atgtgtgcag catcgccaag cggaaccctg | 600 |
| aagccatcac tgaggtcgtc cagctgccca tcacttctc caacagatac tataacagac | 660 |
| ttgtccgaag cctgctggaa tgtgatgaag acacagtcag cacaatcaga dacagcctga | 720 |
| tggagaaaat tgggcctaac atggccagcc tcttccacat cctgcagaca gaccactgtg | 780 |
| cccaaacaca cccacgagct gacttcaaca ggagacgcac caatgagccg cagagctga | 840 |
| aagtcctcct caggaaccct cgaggtgagg aggactctcc ctcccacatc aaacgcacat | 900 |
| cccatgagag tgcataacca gggagaggtt attcacaacc tcaccaaact agtatcattt | 960 |
| tagggggtgtt gacacaccag ttttgagtgt actgtgcctg gtttgatttt tttaaagtag | 1020 |
| ttcctatttt ctatcccct taagaaaat tgcatgaaac taggcttctg taatcaatat | 1080 |
| cccaacattc tgcaatggca gcattcccac caacaaaatc catgtgacca ttctgcctct | 1140 |

```
cctcaggaga aagtaccctc ttttaccaac ttcctctgcc atgttttcc cctgctcccc    1200
tgagaccacc cccaaacaca aaacattcat gtaactctcc agccattgta atttgaagat    1260
gtggatccct ttagaacggt tgccccagta gagttagctg ataaggaaac tttatttaaa    1320
tgcatgtctt aaatgctcat aaagatgtta aatggaattc gtgttatgaa tctgtgctgg    1380
ccatggacga atatgaatgt cacatttgaa ttcttgatct ctaatgagct agtgtcttat    1440
ggtcttgatc ctccaatgtc taattttctt tccgacacat ttaccaaatt gcttgagcct    1500
ggctgtccaa ccagactttg agcctgcatc ttcttgcatc taatgaaaaa caaaaagcta    1560
acatctttac gtactgtaac tgctcagagc tttaaaagta tctttaacaa ttgtcttaaa    1620
accagagaat cttaaggtct aactgtggaa tataaatagc tgaaaactaa tgtactgtac    1680
ataaattcca gaggactctg cttaaacaaa gcagtatata ataactttat tgcatataga    1740
tttagttttg taacttagct ttattttct tttcctggga atggaataac tatctcactt     1800
ccagatatcc acataaatgc tccttgtggc cttttttata actaaggggg tagaagtagt    1860
tttaattcaa catcaaaact taagatgggc ctgtatgaga caggaaaaac caacaggttt    1920
atctgaagga ccccaggtaa gatgttaatc tcccagccca cctcaaccca gaggctactc    1980
ttgacttaga cctatactga agatctctg tcacatccaa ctggaaattc caggaaccaa     2040
aaagagcacc ctatgggctt ggaccactta cagtgtgata aggcctacta tacattagga    2100
agtggcagtt ctttactcgt ccctttcat cggtgcctgg tactctggca aatgatgatg     2160
gggtgggaga ctttccatta aatcaatcag gaatgagtca atcagccttt aggtctttag    2220
tccgggggac ttggggctga gagagtataa ataaccctgg gctgtccagc cttaatagac    2280
ttctcttaca ttttcgtcct gtagcacgct gcctgccaaa gtagtcctgg cagctggacc    2340
atctctgtag gatcgtaaaa aaatagaaan nnnnnnnnn nnnnnnnnnn nnnnnnnnnn     2400
nnnnnctggt ggttgatcat ttctgccatg atgtttacaa gatggcgacc accaangtca    2460
aacgactaac ctatctatga acaacagtag tttctcaggg tcactgtcct tgaacccaac    2520
agtcccttat gagcgtcact gcccaccaaa ggtcaatgtc aagagaggaa gagagggagg    2580
aggggtagga ctgcaggggc cactccaaac tcgcttaggt agaaactatt ggtgcttgac    2640
tctcactagg ctaaactcaa gatttgacca aatcgagtga tagggatcct ggtgggagga    2700
gagagggcac atctccagaa aaatgaaaag caatacaact ttaccataaa gcctttaaaa    2760
ccagtaacgt gctgctcaag gaccaagagc aattnnnnnn nnnnnnnnnn nnnnnnnnnn    2820
nnnncaaaca ttgctgcctt tgtccccaca cagcctctaa gcgtgctgac atcagattgt    2880
taagggcatt tttatactca gaactgtccc atccccaggt ccccaaactt atggacactg    2940
ccttagcctc ttggaaatca ggtagaccat attctaagtt agactcttcc cctccctccc    3000
acacttccca cccccaggca aggctgactt ctctgaatca gaaaagctat taaagtttgt    3060
gtgttgtgtc cattttgcaa acccaactaa gccaggaccc caatgcgaca gtagttcat     3120
gagtattcct agcaaatttc tctctttctt cagttcagta gatttccttt tttcttntct    3180
nttntttttt ntttttttgg ctgtgacctc ttcaaaccgt ggtaccccc cttttctccc     3240
cacgatgata tctatatatg tatctacaat acatatatct acacatacag aaagaagcag    3300
ttctcacaat gttgctagtt ttttgcttct ctttccccca ccctactccc tccaattccc    3360
ccttaaactt ccaaagcttc gtcttgtgtt gctgcagag tgattcgggg gctgacctag     3420
accagtttgc atgattcttc tcttgtgatt tggttgcact ttagacattt ttgtgccatt    3480
```

```
atatttgcat tatgtattta taatttaaat gatatttagg ttttggctg agtactggaa    3540 taaacagtga gcatatctgg tatatgtcat tatttattgt taaattacat ttttaagctc    3600
catgtgcata taaggttat gaaacatatc atggtaatga cagatgcaag ttattttatt    3660
tgcttatttt tataattaaa gatgccatag cataaatga agcctttggt gaattccttc    3720
taagataaaa ataataataa agtgttacgt tttattggtt tc                      3762
```

<210> SEQ ID NO 3
<211> LENGTH: 247
<212> TYPE: PRT
<213> ORGANISM: Homo sapiens

<400> SEQUENCE: 3

```
Met Leu Gln Asn Ser Ala Val Leu Leu Val Leu Val Ile Ser Ala Ser
 1               5                  10                  15

Ala Thr His Glu Ala Glu Gln Asn Asp Ser Val Ser Pro Arg Lys Ser
            20                  25                  30

Arg Val Ala Ala Gln Asn Ser Ala Glu Val Val Arg Cys Leu Asn Ser
        35                  40                  45

Ala Leu Gln Val Gly Cys Gly Ala Phe Ala Cys Leu Glu Asn Ser Thr
    50                  55                  60

Cys Asp Thr Asp Gly Met Tyr Asp Ile Cys Lys Ser Phe Leu Tyr Ser
65                  70                  75                  80

Ala Ala Lys Phe Asp Thr Gln Gly Lys Ala Phe Val Lys Glu Ser Leu
                85                  90                  95

Lys Cys Ile Ala Asn Gly Val Thr Ser Lys Val Phe Leu Ala Ile Arg
            100                 105                 110

Arg Cys Ser Thr Phe Gln Arg Met Ile Ala Glu Val Gln Glu Glu Cys
        115                 120                 125

Tyr Ser Lys Leu Asn Val Cys Ser Ile Ala Lys Arg Asn Pro Glu Ala
    130                 135                 140

Ile Thr Glu Val Val Gln Leu Pro Asn His Phe Ser Asn Arg Tyr Tyr
145                 150                 155                 160

Asn Arg Leu Val Arg Ser Leu Leu Glu Cys Asp Glu Asp Thr Val Ser
                165                 170                 175

Thr Ile Arg Asp Ser Leu Met Glu Lys Ile Gly Pro Asn Met Ala Ser
            180                 185                 190

Leu Phe His Ile Leu Gln Thr Asp His Cys Ala Gln Thr His Pro Arg
        195                 200                 205

Ala Asp Phe Asn Arg Arg Thr Asn Glu Pro Gln Lys Leu Lys Val
    210                 215                 220

Leu Leu Arg Asn Leu Arg Gly Glu Glu Asp Ser Pro Ser His Ile Lys
225                 230                 235                 240

Arg Thr Ser His Glu Ser Ala
                245
```

<210> SEQ ID NO 4
<211> LENGTH: 20
<212> TYPE: DNA
<213> ORGANISM: Homo sapiens

<400> SEQUENCE: 4

```
tctaggtcag cccccgaatc                                                  20
```

<210> SEQ ID NO 5
<211> LENGTH: 22

```
<212> TYPE: DNA
<213> ORGANISM: Homo sapiens

<400> SEQUENCE: 5
cctccaattc cccttaaac tt                                              22
```

METHOD OF DIAGNOSING, MONITORING, STAGING, IMAGING AND TREATING CANCER

INTRODUCTION

This application is a Divisional Application of U.S. patent application Ser. No. 09/705,500 filed Nov. 3, 2000 now U.S. Pat. No. 6,902,890, which claims the benefit of priority to U.S. Provisional Application Ser. No. 60/163,444, filed Nov. 4, 1999, each of which are herein incorporated by reference in their entirety.

This application claims the benefit of provisional U.S. Application Ser. No. 60/163,444, filed Nov. 4, 1999.

FIELD OF THE INVENTION

This invention relates, in part, to newly developed assays for detecting, diagnosing, monitoring, staging, prognosticating, imaging and treating cancers, particularly lung cancer.

BACKGROUND OF THE INVENTION

Lung cancer is the second most prevalent type of cancer for both men and women in the United States and is the most common cause of cancer death in both sexes. Lung cancer can result from a primary tumor originating in the lung or a secondary tumor which has spread from another organ such as the bowel or breast. Primary lung cancer is divided into three main types; small cell lung cancer; non-small cell lung cancer; and mesothelioma. Small cell lung cancer is also called "Oat Cell" lung cancer because the cancer cells are a distinctive oat shape. There are three types of non-small cell lung cancer. These are grouped together because they behave in a similar way and respond to treatment differently to small cell lung cancer. The three types are squamous cell carcinoma, adenocarcinoma, and large cell carcinoma. Squamous cell cancer is the most common type of lung cancer. It develops from the cells that line the airways. Adenocarcinoma also develops from the cells that line the airways. However, adenocarcinoma develops from a particular type of cell that produces mucus (phlegm). Large cell lung cancer has been thus named because the cells look large and rounded when they are viewed under a microscope. Mesothelioma is a rare type of cancer which affects the covering of the lung called the pleura. Mesothelioma is often caused by exposure to asbestos.

Secondary lung cancer is cancer that has started somewhere else in the body (for example, the breast or bowel) and spread to the lungs. Choice of treatment for secondary lung cancer depends on where the cancer started. In other words, cancer that has spread from the breast should respond to breast cancer treatments and cancer that has spread from the bowel should respond to bowel cancer treatments.

The stage of a cancer indicates how far a cancer has spread. Staging is important because treatment is often decided according to the stage of a cancer. The staging is different for non-small cell and for small cell cancers of the lung.

Non-small cell cancer can be divided into four stages. Stage I is very localized cancer with no cancer in the lymph nodes. Stage II cancer has spread to the lymph nodes at the top of the affected lung. Stage III cancer has spread near to where the cancer started. This can be to the chest wall, the covering of the lung (pleura), the middle of the chest (mediastinum) or other lymph nodes. Stage IV cancer has spread to another part of the body.

Since small cell lung cancer can spreads quite early in development of the disease, small cell lung cancers are divided into only two groups. These are: limited disease, that is cancer that can only be seen in one lung and in nearby lymph nodes; and extensive disease, that is cancer that has spread outside the lung to the chest or to other parts of the body. Further, even if spreading is not apparent on the scans, it is likely that some cancer cells will have broken away and traveled through the bloodstream or lymph system. To be safe, it is therefore preferred to treat small cell lung cancers as if they have spread, whether or not secondary cancer is visible. Because surgery is not typically used to treat small cell cancer, except in very early cases, the staging is not as critical as it is with some other types of cancer. Chemotherapy with or without radiotherapy is often employed. The scans and tests done at first will be used later to see how well a patient is responding to treatment.

Procedures used for detecting, diagnosing, monitoring, staging, and prognosticating lung cancer are of critical importance to the outcome of the patient. For example, patients diagnosed with early lung cancer generally have a much greater five-year survival rate as compared to the survival rate for patients diagnosed with distant metastasized lung cancer. New diagnostic methods which are more sensitive and specific for detecting early lung cancer are clearly needed.

Lung cancer patients are closely monitored following initial therapy and during adjuvant therapy to determine response to therapy and to detect persistent or recurrent disease of metastasis. There is clearly a need for a lung cancer marker which is more sensitive and specific in detecting lung cancer, its recurrence and progression.

Another important step in managing lung cancer is to determine the stage of the patient's disease. Stage determination has potential prognostic value and provides criteria for designing optimal therapy. Generally, pathological staging of lung cancer is preferable over clinical staging because the former gives a more accurate prognosis. However, clinical staging would be preferred were it at least as accurate as pathological staging because it does not depend on an invasive procedure to obtain tissue for pathological evaluation. Staging of lung cancer would be improved by detecting new markers in cells, tissues, or bodily fluids which could differentiate between different stages of invasion.

U.S. Pat. No. 5,877,290 and U.S. Pat. No. 5,837,498, which are incorporated herein by reference, disclose a human Corpuscles of Stannius, staniocalcin polypeptide and the nucleic acid sequence encoding this polypeptide. Also disclosed are methods of using this polypeptide for therapeutic purposes such as treatment of electrolyte disorders and disorders due to elevated bone resorption.

It has now been found that this polypeptide and the nucleic acid encoding this polypeptide, which are referred to herein as Lng108 are diagnostic markers for cancer. Accordingly, in the present invention methods are provided for detecting, diagnosing, monitoring, staging, prognosticating, in vivo imaging and treating cancer via Lng108. Lng108 refers, among other things, to native proteins expressed by the gene comprising the polynucleotide sequence of SEQ ID NO:1 or 2. The deduced amino acid sequence of a polypeptide encoded thereby is depicted in SEQ ID NO:3. By "Lng108" it is also meant herein polynucleotides which, due to degeneracy in genetic coding, comprise variations in nucleotide sequence as compared to SEQ ID NO: 1 or 2, but which still encode the same protein. In the alternative, what is meant by Lng108 as used herein, means the native mRNA encoded by the gene comprising SEQ ID NO:1 or 2 or it can refer to the actual gene comprising SEQ ID NO:1 or 2, or levels of a polynucleotide which is capable of hybridizing under stringent conditions to the antisense sequence of SEQ ID NO:1 or 2.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

SUMMARY OF THE INVENTION

Toward these ends, and others, it is an object of the present invention to provide a method for diagnosing the presence cancer by analyzing for changes in levels of Lng108 in cells, tissues or bodily fluids compared with levels of Lng108 in preferably the same cells, tissues, or bodily fluid type of a normal human control, wherein a change in levels of Lng108 in the patient versus the normal human control is associated with cancer.

Further provided is a method of diagnosing metastatic cancer in a patient having cancer which is not known to have metastasized by identifying a human patient suspected of having cancer that has metastasized; analyzing a sample of cells, tissues, or bodily fluid from such patient for Lng108; comparing the Lng108 levels in such cells, tissues, or bodily fluid with levels of Lng108 in preferably the same cells, tissues, or bodily fluid type of a normal human control, wherein an increase in Lng108 levels in the patient versus the normal human control is associated with cancer which has metastasized.

Also provided by the invention is a method of staging cancer in a human with cancer by identifying a human patient having cancer; analyzing a sample of cells, tissues, or bodily fluid from such patient for Lng108; comparing Lng108 levels in such cells, tissues, or bodily fluid with levels of Lng108 in preferably the same cells, tissues, or bodily fluid type of a normal human control sample, wherein an increase in Lng108 levels in the patient versus the normal human control is associated with a cancer which is progressing and a decrease in the levels of Lng108 is associated with a cancer which is regressing or in remission.

Further provided is a method of monitoring cancer in a human patient for the onset of metastasis. The method comprises identifying a human patient having cancer that is not known to have metastasized; periodically analyzing a sample of cells, tissues, or bodily fluid from such patient for Lng108; comparing the Lng108 levels in such cells, tissue, or bodily fluid with levels of Lng108 in preferably the same cells, tissues, or bodily fluid type of a normal human control sample, wherein an increase in Lng108 levels in the patient versus the normal human control is associated with a cancer which has metastasized.

Further provided is a method of monitoring the change in stage of cancer in a human patient by looking at levels of Lng108 in the human patient. The method comprises identifying a human patient having cancer; periodically analyzing a sample of cells, tissues, or bodily fluid from such patient for Lng108; comparing the Lng108 levels in such cells, tissue, or bodily fluid with levels of Lng108 in preferably the same cells, tissues, or bodily fluid type of a normal human control sample, wherein an increase in Lng108 levels in the patient versus the normal human control is associated with a cancer which is progressing and a decrease in the levels of Lng108 is associated with a cancer which is regressing or in remission.

Further provided are methods of designing new therapeutic agents targeted to Lng108 for use in imaging and treating cancer. For example, in one embodiment, therapeutic agents such as antibodies targeted against Lng108 or fragments of such antibodies can be used to detect or image localization of Lng108 in a patient for the purpose of detecting or diagnosing a disease or condition. Such antibodies can be polyclonal, monoclonal, or omniclonal or prepared by molecular biology techniques. The term "antibody", as used herein and throughout the instant specification is also meant to include aptamers and single-stranded oligonucleotides such as those derived from an in vitro evolution protocol referred to as SELEX and well known to those skilled in the art. Antibodies can be labeled with a variety of detectable labels including, but not limited to, radioisotopes and paramagnetic metals. Therapeutics agents such as small molecules and antibodies which decrease the concentration and/or activity of Lng108 can also be used in the treatment of diseases characterized by expression of Lng108. Such agents can be readily identified in accordance with the teachings herein.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

DESCRIPTION OF THE INVENTION

The present invention relates to diagnostic assays and methods, both quantitative and qualitative for detecting, diagnosing, monitoring, staging, prognosticating, in vivo imaging and treating cancers by comparing levels of Lng108 with those of Lng108 in a normal human control. Lng108 refers, among other things, to native proteins expressed by the gene comprising the polynucleotide sequence of SEQ ID NO:1 or 2. The deduced amino acid sequence of a polypeptide encoded thereby is depicted in SEQ ID NO:3. By "Lng108" it is also meant herein polynucleotides which, due to degeneracy in genetic coding, comprise variations in nucleotide sequence as compared to SEQ ID NO: 1 or 2, but which still encode the same protein. In the alternative, what is meant by Lng108 as used herein, means the native mRNA encoded by the gene comprising SEQ ID NO:1 or 2 or it can refer to the actual gene comprising SEQ ID NO:1 or 2, or levels of a polynucleotide which is capable of hybridizing under stringent conditions to the antisense sequence of SEQ ID NO:1 or 2. Such levels are preferably measured in at least one of, cells, tissues and/or bodily fluids, including determination of normal and abnormal levels. Thus, for instance, a diagnostic assay in accordance with the invention for diagnosing over-expression of Lng108 protein compared to normal control bodily fluids, cells, or tissue samples may be used to diagnose the presence of cancers, including lung cancer. Lng108 may be measured alone in the methods of the invention, or, more preferably, in combination with other diagnostic markers for cancer. Thus, it is preferred that the methods of the present invention be employed in combination with measurement of the levels of other cancer markers as well as Lng108. Other cancer markers, in addition to Lng108, useful in the present invention will depend on the cancer being tested and are known to those of skill in the art.

Detection of Lng108 is particularly useful in lung cancer. However, this marker is also useful in the diagnosis, prognosis, staging, imaging and treatment of other types of cancer.

Diagnostic Assays

The present invention provides methods for diagnosing the presence of cancer, including lung cancer, by analyzing for changes in levels of Lng108 in cells, tissues or bodily fluids compared with levels of Lng108 in cells, tissues or bodily fluids of preferably the same type from a normal human control, wherein an increase in levels of Lng108 in the patient versus the normal human control is associated with the presence of cancer.

Without limiting the instant invention, typically, for a quantitative diagnostic assay a positive result indicating the patient being tested has cancer is one in which cells, tissues, or bodily fluid levels of a cancer marker, such as Lng108, are at least two times higher, and most preferable are at least five times higher, than in preferably the same cells, tissues, or bodily fluid of a normal human control.

The present invention also provides a method of diagnosing metastatic cancer, including metastatic lung cancer, in a patient having a cancer which has not yet metastasized. In the method of the present invention, a human cancer patient suspected of having cancer which may have metastasized (but which was not previously known to have metastasized) is identified. This is accomplished by a variety of means known to those of skill in the art.

In the present invention, determining the presence of Lng108 in cells, tissues, or bodily fluid, is particularly useful for discriminating between cancers which have not metastasized and cancers which have metastasized. Existing techniques have difficulty discriminating between a cancer which has metastasized and a cancer which has not metastasized and proper treatment selection is often dependent upon such knowledge.

In the present invention, one of the cancer marker levels measured in cells, tissues, or bodily fluid of a human patient is Lng108. Levels in the human patient are compared with levels of Lng108 in preferably the same cells, tissue, or bodily fluid type of a normal human control. That is, if the cancer marker being observed is Lng108 in serum, this level is preferably compared with the level of Lng108 in serum of a normal human control. An increase in Lng108 in the human patient versus the normal human control is associated with a cancer which has metastasized.

Without limiting the instant invention, typically, for a quantitative diagnostic assay a positive result indicating the cancer in the patient being tested or monitored has metastasized is one in which cells, tissues, or bodily fluid levels of a cancer marker, such as Lng108, are at least two times higher, and more preferably are at least five times higher, than in preferably the same cells, tissues, or bodily fluid of a normal human control.

Normal human control as used herein includes a human patient without cancer and/or non cancerous samples from the patient; in the methods for diagnosing or monitoring for metastasis, normal human control may preferably also include samples from a human patient that is determined by reliable methods to have a cancer such as lung cancer which has not metastasized.

Staging

The invention also provides a method of staging cancers in a human patient. The method comprises identifying a human patient having cancer and analyzing a sample of cells, tissues, or bodily fluid from such patient for Lng108. The measured Lng108 levels are then compared to levels of Lng108 in preferably the same cells, tissues, or bodily fluid type of a normal human control, wherein an increase in Lng108 levels in the human patient versus the normal human control is associated with a cancer which is progressing and a decrease in the levels of Lng108 is associated with a cancer which is regressing or in remission.

Monitoring

Further provided is a method of monitoring cancer in a human patient for the onset of metastasis. The method comprises identifying a human patient having cancer that is not known to have metastasized; periodically analyzing cells, tissues, or bodily fluid from such patient for Lng108; and comparing the Lng108 levels in such cells, tissue, or bodily fluid with levels of Lng108 in preferably the same cells, tissues, or bodily fluid type of a normal human control, wherein an increase in Lng108 levels in the patient versus the normal human control is associated with a cancer which has metastasized.

Further provided by this invention is a method of monitoring the change in stage of a cancer. The method comprises identifying a human patient having cancer; periodically analyzing cells, tissues, or bodily fluid from such patient for Lng108; and comparing the Lng108 levels in such cells, tissue, or bodily fluid with levels of Lng108 in preferably the same cells, tissues, or bodily fluid type of a normal human control, wherein an increase in Lng108 levels in the patient versus the normal human control is associated with a cancer which is progressing in stage and a decrease in the levels of Lng108 is associated with a cancer which is regressing in stage or in remission.

Monitoring such patients for onset of metastasis is periodic and preferably done on a quarterly basis. However, this may be performed more or less frequent depending on the cancer, the particular patient, and the stage of the cancer.

Prognostic Testing and Clinical Trial Monitoring

The methods described herein can further be utilized as prognostic assays to identify subjects having or at risk of developing a disease or disorder associated with increased levels of Lng108. The present invention provides a method in which a test sample is obtained from a human patient and Lng108 is detected. The presence of higher Lng108 levels as compared to normal human controls is diagnostic for the human patient being at risk for developing cancer, particularly lung cancer.

The effectiveness of therapeutic agents to decrease expression or activity of Lng108 can also be monitored by analyzing levels of expression of Lng108 in a human patient in clinical trials or in in vitro screening assays such as in human cells. In this way, the gene expression pattern can serve as a marker, indicative of the physiological response of the human patient, or cells as the case may be, to the agent being tested.

Detection of Genetic Lesions or Mutations

The methods of the present invention can also be used to detect genetic lesions or mutations in Lng108, thereby determining if a human with the genetic lesion is at risk for cancer or has cancer, particularly lung cancer. Genetic lesions can be detected, for example, by ascertaining the existence of a deletion and/or addition and/or substitution of one or more nucleotides from Lng108, a chromosomal rearrangement of Lng108, aberrant modification of Lng108 (such as of the methylation pattern of the genomic DNA), the presence of a non-wild type splicing pattern of a mRNA transcript of Lng108, allelic loss of Lng108, and/or inappropriate post-translational modification of Lng108 protein. Methods to detect such lesions in Lng108 are known to those of skill in the art.

Assay Techniques

Assay techniques that can be used to determine levels of gene expression, such as Lng108 of the present invention, in a sample derived from a human are well-known to those of skill in the art. Such assay methods include radioimmunoassays, reverse transcriptase PCR (RT-PCR) assays, immunohistochemistry assays, in situ hybridization assays, competitive-binding assays, Western Blot analyses, ELISA assays and proteomic approaches. Among these, ELISAs are frequently preferred to diagnose a gene's expressed protein in biological fluids.

An ELISA assay initially comprises preparing an antibody, if not readily available from a commercial source, specific to Lng108, preferably a monoclonal antibody. In addition a reporter antibody generally is prepared which binds specifically to Lng108. The reporter antibody is attached to a detectable reagent such as a radioactive, fluorescent or enzymatic reagent, for example horseradish peroxidase enzyme or alkaline phosphatase.

To carry out the ELISA, antibody specific to Lng108 is incubated on a solid support, e.g., a polystyrene dish, that binds the antibody. Any free protein binding sites on the dish are then covered by incubating with a non-specific protein such as bovine serum albumin. Next, the sample to be analyzed is incubated in the dish, during which time Lng108 binds to the specific antibody attached to the polystyrene dish. Unbound sample is washed out with buffer. A reporter antibody specifically directed to Lng108 and linked to a detectable reagent such as horseradish peroxidase is placed in the dish resulting in binding of the reporter antibody to any monoclonal antibody bound to Lng108. Unattached reporter antibody is then washed out. Reagents for peroxidase activity, including a colorimetric substrate are then added to the dish. Immobilized peroxidase, linked to Lng108 antibodies, produces a colored reaction product. The amount of color developed in a given time period is proportional to the amount of Lng108 protein present in the sample. Quantitative results typically are obtained by reference to a standard curve.

A competition assay can also be employed wherein antibodies specific to Lng108 are attached to a solid support and labeled Lng108 and a sample derived from the patient or human control are passed over the solid support. The amount of label detected which is attached to the solid support can be correlated to a quantity of Lng108 in the sample.

Using all or a portion of the nucleic acid sequence for Lng108 as a hybridization probe, nucleic acid methods can also be used to detect Lng108 mRNA as a marker for cancer, including lung cancer. Polymerase chain reaction (PCR) and other nucleic acid methods, such as ligase chain reaction (LCR) and nucleic acid sequence based amplification (NASABA), can be used to detect malignant cells for diagnosis and monitoring of various malignancies. For example, reverse-transcriptase PCR (RT-PCR) is a powerful technique which can be used to detect the presence of a specific mRNA population in a complex mixture of thousands of other mRNA species. In RT-PCR, an mRNA species is first reverse transcribed to complementary DNA (cDNA) with use of the enzyme reverse transcriptase; the cDNA is then amplified as in a standard PCR reaction. RT-PCR can thus reveal by amplification the presence of a single species of mRNA. Accordingly, if the mRNA is highly specific for the cell that produces it, RT-PCR can be used to identify the presence of a specific type of cell.

Hybridization to clones or oligonucleotides arrayed on a solid support (i.e., gridding) can be used to both detect the expression of and quantitate the level of expression of that gene. In this approach, a cDNA encoding the Lng108 gene is fixed to a substrate. The substrate may be of any suitable type including but not limited to glass, nitrocellulose, nylon or plastic. At least a portion of the DNA encoding the Lng108 gene is attached to the substrate and then incubated with the analyte, which may be RNA or a complementary DNA (cDNA) copy of the RNA, isolated from the tissue of interest. Hybridization between the substrate bound DNA and the analyte can be detected and quantitated by several means including but not limited to radioactive labeling or fluorescence labeling of the analyte or a secondary molecule designed to detect the hybrid. Quantitation of the level of gene expression can be done by comparison of the intensity of the signal from the analyte compared with that determined from known standards. The standards can be obtained by in vitro transcription of the target gene, quantitating the yield, and then using that material to generate a standard curve.

Of the proteomic approaches, 2D electrophoresis is a technique well known to those in the art. Isolation of individual proteins from a sample such as serum is accomplished using sequential separation of proteins by different characteristics usually on polyacrylamide gels. First, proteins are separated by size using an electric current. The current acts uniformly on all proteins, so smaller proteins move farther on the gel than larger proteins. The second dimension applies a current perpendicular to the first and separates proteins not on the basis of size but on the specific electric charge carried by each protein. Since no two proteins with different sequences are identical on the basis of both size and charge, the result of a 2D separation is a square gel in which each protein occupies a unique spot. Analysis of the spots with chemical or antibody probes, or subsequent protein microsequencing can reveal the relative abundance of a given protein and the identity of the proteins in the sample.

The above tests can be carried out on samples derived from a variety cells, bodily fluids and/or tissue extracts (homogenates or solubilized tissue) obtained from the patient including tissue biopsy and autopsy material. Bodily fluids useful in the present invention include blood, urine, saliva, or any other bodily secretion or derivative thereof. Blood can include whole blood, plasma, serum, or any derivative of blood.

In Vivo Targeting of Lng108/Cancer Therapy

Identification of Lng108 is also useful in the rational design of new therapeutics for imaging and treating cancers, and in particular lung cancer. For example, in one embodiment, antibodies which specifically bind to Lng108 can be raised and used in vivo in patients suspected of suffering from cancer. Antibodies which specifically bind a Lng108 can be injected into a patient suspected of having cancer for diagnostic and/or therapeutic purposes. Thus, another aspect of the present invention provides for a method for preventing the onset and treatment of lung cancer in a human patient in need of such treatment by administering to the patient an effective amount of an antibody. By "effective amount" it is meant the amount or concetration of antibody needed to bind to the target antigens expressed on the tumor to cause tumor shrinkage for surgical removal, or disappearance of the tumor. The binding of the antibody to Lng108 is believed to cause the death of the cancer cell expressing such Lng108. The preparation and use of antibodies for in vivo diagnosis is well known in the art. For example, antibody-chelators labeled with Indium-111 have been described for use in the radioimmunoscintographic imaging of carcinoembryonic antigen expressing tumors (Sumerdon et al. Nucl. Med. Biol. 1990 17:247-254). In particular, these antibody-chelators have been used in detecting tumors in patients suspected of having recurrent colorectal cancer (Griffin et al. J. Clin. Onc. 1991 9:631-640). Antibodies with paramagnetic ions as labels for use in magnetic resonance imaging have also been described (Lauffer, R. B. Magnetic Resonance in Medicine 1991 22:339-342). Antibodies directed against Lng108 can be used in a similar manner. Labeled antibodies which specifically bind Lng108 can be injected into patients suspected of having cancer for the purpose of diagnosing or staging of the disease status of the patient. The label used will be selected in accordance with the imaging modality to be used. For example, radioactive labels such as Indium-111, Technetium-99m or Iodine-131 can be used for planar scans or single photon emission computed tomography (SPECT). Positron emitting labels such as Fluorine-19 can be used in positron emission tomography. Paramagnetic ions such as Gadlinium (III) or Manganese (II) can be used in magnetic resonance imaging (MRI). Localization of the label permits determination of the spread of the cancer. The amount of label within an organ or tissue also allows determination of the presence or absence of cancer in that organ or tissue.

Antibodies which can be used in in vivo methods include polyclonal, monoclonal and omniclonal antibodies and antibodies prepared via molecular biology techniques. Antibody fragments and aptamers and single-stranded oligonucleotides such as those derived from an in vitro evolution protocol referred to as SELEX and well known to those skilled in the art can also be used.

Screening Assays

The present invention also provides methods for identifying modulators which bind to Lng108 protein or have a modulatory effect on the expression or activity of Lng108 protein. Modulators which decrease the expression or activity of Lng108 protein are believed to be useful in treating cancer, particularly lung cancer. Such screening assays are known to those of skill in the art and include, without limitation, cell-based assays and cell free assays.

Small molecules predicted via computer imaging to specifically bind to regions of Lng108 can also be designed, synthesized and tested for use in the imaging and treatment of cancer. Further, libraries of molecules can be screened for potential anticancer agents by assessing the ability of the molecule to bind to Lng108. Molecules identified in the library as being capable of binding to Lng108 are key candidates for further evaluation for use in the treatment of cancer, particularly lung cancer. In a preferred embodiment, these molecules will downregulate expression and/or activity of Lng108 in cells.

Adoptive Immunotherapy and Vaccines

Adoptive immunotherapy of cancer refers to a therapeutic approach in which immune cells with an antitumor reactivity are administered to a tumor-bearing host, with the aim that the cells mediate either directly or indirectly, the regression of an established tumor. Transfusion of lymphocytes, particularly T lymphocytes, falls into this category and investigators at the National Cancer Institute (NCI) have used autologous reinfusion of peripheral blood lymphocytes or tumor-infiltrating lymphocytes (TIL), T cell cultures from biopsies of subcutaneous lymph nodules, to treat several human cancers (Rosenberg, S. A., U.S. Pat. No. 4,690,914, issued Sep. 1, 1987; Rosenberg, S. A., et al., 1988, N. England J. Med. 319:1676-1680).

The present invention relates to compositions and methods of adoptive immunotherapy for the prevention and/or treatment of primary and metastatic cancer in humans using macrophages sensitized to the antigenic Lng108 molecules, with or without non-covalent complexes of heat shock protein (hsp). Antigenicity or immunogenicity of Lng108 is readily confirmed by the ability of the Lng108 protein or a fragment thereof to raise antibodies or educate naive effector cells, which in turn lyse target cells expressing the antigen (or epitope).

Cancer cells are, by definition, abnormal and contain proteins which should be recognized by the immune system as foreign since they are not present in normal tissues. However, the immune system often seems to ignore this abnormality and fails to attack tumors. The foreign Lng108 proteins that are produced by the cancer cells can be used to reveal their presence. The Lng108 is broken into short fragments, called tumor antigens, which are displayed on the surface of the cell. These tumor antigens are held or presented on the cell surface by molecules called MHC, of which there are two types: class I and II. Tumor antigens in association with MHC class I molecules are recognized by cytotoxic T cells while antigen-MHC class II complexes are recognized by a second subset of T cells called helper cells. These cells secrete cytokines which slow or stop tumor growth and help another type of white blood cell, B cells, to make antibodies against the tumor cells.

In adoptive immunotherapy, T cells or other antigen presenting cells (APCs) are stimulated outside the body (ex vivo), using the tumor specific Lng108 antigen. The stimulated cells are then reinfused into the patient where they attack the cancerous cells. Research has shown that using both cytotoxic and helper T cells is far more effective than using either subset alone. Additionally, the Lng108 antigen may be complexed with heat shock proteins to stimulate the APCs as described in U.S. Pat. No. 5,985,270.

The APCs can be selected from among those antigen presenting cells known in the art including, but not limited to, macrophages, dendritic cells, B lymphocytes, and a combination thereof, and are preferably macrophages. In a preferred use, wherein cells are autologous to the individual, autologous immune cells such as lymphocytes, macrophages or other APCs are used to circumvent the issue of whom to select as the donor of the immune cells for adoptive transfer. Another problem circumvented by use of autologous immune cells is graft versus host disease which can be fatal if unsuccessfully treated.

In adoptive immunotherapy with gene therapy, DNA of the Lng108 can be introduced into effector cells similarly as in conventional gene therapy. This can enhance the cytotoxicity of the effector cells to tumor cells as they have been manipulated to produce the antigenic protein resulting in improvement of the adoptive immunotherapy.

Lng108 antigens of this invention are also useful as components of cancer vaccines. The vaccine comprises an immunogenically stimulatory amount of a Lng108 antigen. Immunogenically stimulatory amount refers to that amount of antigen that is able to invoke the desired immune response in the recipient for the amelioration, or treatment of cancer, particularly lung cancer. Effective amounts may be determined empirically by standard procedures well known to those skilled in the art.

The Lng108 antigen may be provided in any one of a number of vaccine formulations which are designed to induce the desired type of immune response, e.g., antibody and/or cell mediated. Such formulations are known in the art and include, but are not limited to, formulations such as those described in U.S. Pat. No. 5,585,103. Vaccine formulations of the present invention used to stimulate immune responses can also include pharmaceutically acceptable adjuvants.

EXAMPLE

The present invention is further described by the following example. The example is provided solely to illustrate the invention by reference to specific embodiments. This exemplification, while illustrating certain specific aspects of the invention, does not portray the limitations or circumscribe the scope of the disclosed invention.

Experiments described herein were carried out using standard techniques, which are well known and routine to those of skill in the art, except where otherwise described in detail. Routine molecular biology techniques were carried out as described in standard laboratory manuals, such as Sambrook et al., MOLECULAR CLONING: A LABORATORY MANUAL, 2nd Ed.; Cold Spring Harbor Laboratory Press, Cold Spring Harbor, N.Y. (1989).

Relative Quantitation of Gene Expression

Real-Time quantitative PCR with fluorescent Taqman probes is a quantitation detection system utilizing the 5'-3' nuclease activity of Taq DNA polymerase. The method uses an internal fluorescent oligonucleotide probe (Taqman) labeled with a 5' reporter dye and a downstream, 3' quencher dye. During PCR, the 5'-3' nuclease activity of Taq DNA polymerase releases the reporter, whose fluorescence can then be detected by the laser detector of the Model 7700 Sequence Detection System (PE Applied Biosystems, Foster City, Calif., USA).

Amplification of an endogenous control was used to standardize the amount of sample RNA added to the reaction and normalize for Reverse Transcriptase (RT) efficiency. Either cyclophilin, glyceraldehyde-3-phosphate dehydrogenase (GAPDH) or 18S ribosomal RNA (rRNA) was used as this endogenous control. To calculate relative quantitation between all the samples studied, the target RNA levels for one sample were used as the basis for comparative results (calibrator). Quantitation relative to the "calibrator" can be obtained using the standard curve method or the comparative method (User Bulletin #2: ABI PRISM 7700 Sequence Detection System).

The tissue distribution, and the level of the target gene for every example in normal and cancer tissue were determined. Total RNA was extracted from normal tissues, cancer tissues, and from cancers and the corresponding matched adjacent tissues. Subsequently, first strand cDNA was prepared with reverse transcriptase and the polymerase chain reaction was done using primers and Taqman probe specific to each target gene. The results are analyzed using the ABI PRISM 7700 Sequence Detector. The absolute numbers are relative levels of expression of the target gene in a particular tissue compared to the calibrator tissue.

Primers used for expression analysis include:

```
5' TCTAGGTCAGCCCCCGAATC 3';      (SEQ ID NO:4)
and

5' CCTCCAATTCCCCCTTAAACTT 3'.    (SEQ ID NO:5)
```

The absolute numbers depicted in Table 1 are relative levels of expression of Lng108 (also referred to as Clone ID 954287; Gene ID 21300) in 12 normal different tissues. All the values are compared to normal muscle (calibrator). These RNA samples are commercially available pools, originated by pooling samples of a particular tissue from different individuals.

TABLE 1

Relative Levels of Lng108 Expression in Pooled Samples

| TISSUE | NORMAL |
|---|---|
| Brain | 0.57 |
| Heart | 1.63 |
| Kidney | 9.55 |
| Liver | 0.38 |
| Lung | 53.46 |
| Mammary Gland | 13.00 |
| Muscle | 1.00 |
| Prostate | 1.69 |
| Small Intestine | 0.80 |
| Testis | 0.56 |
| Thymus | 1.06 |
| Uterus | 4.88 |

The relative levels of expression in Table 1 show that Lng108 mRNA is expressed in all 12 tissue types analyzed. The expression level of Lng108 is relatively higher in lung and is lower in brain, liver, small intestine and testis and is medium in kidney, mammary gland and uterus. These results demonstrate that Lng108 mRNA expression is not restricted to lung tissue but is expressed broadly in all tissue types analyzed.

The absolute numbers in Table 1 were obtained analyzing pools of samples of a particular tissue from different individuals. They can not be compared to the absolute numbers originated from RNA obtained from tissue samples of a single individual in Table 2.

The absolute numbers depicted in Table 2 are relative levels of expression of Lng108 in 48 pairs of matching samples and 2 cancer and 2 normal/normal adjacent tissues of ovary. All the values are compared to normal muscle (calibrator). A matching pair is formed by mRNA from the cancer sample for a particular tissue and mRNA from the normal adjacent sample for that same tissue from the same individual.

TABLE 2

Relative Levels of Lng108 Expression in Individual Samples

| Sample ID | Cancer Type | Tissue | Cancer | Matching Normal Adjacent |
|---|---|---|---|---|
| LngAC82 | Adenocarcinoma | Lung 1 | 29.75 | 28.15 |
| Lng60XL | Adenocarcinoma | Lung 2 | 28.9 | 5.3 |
| LngAC66 | Adenocarcinoma | Lung 3 | 5.01 | 5.50 |
| LngAC69 | Adenocarcinoma | Lung 4 | 58.28 | 15.19 |
| LngAC88 | Adenocarcinoma | Lung 5 | 90.20 | 111.0 |
| LngAC13 | Adenocarcinoma | Lung 6 | 18.32 | 0.00 |
| LngSQ9X | Squamous cell carcinoma | Lung 7 | 57.88 | 9.09 |

TABLE 2-continued

Relative Levels of Lng108 Expression in Individual Samples

| Sample ID | Cancer Type | Tissue | Cancer | Matching Normal Adjacent |
|---|---|---|---|---|
| LngQ45 | Squamous cell carcinoma | Lung 8 | 31 | 76 |
| LngSQ56 | Squamous cell carcinoma | Lung 9 | 56 | 65 |
| LngSQ32 | Squamous cell carcinoma | Lung 10 | 3821.7 | 218.3 |
| LngSQ79 | Squamous cell carcinoma | Lung 11 | 574.04 | 467.88 |
| LngC20X | Squamous cell carcinoma | Lung 12 | 0.7 | 0.4 |
| Lng47XQ | Squamous cell carcinoma | Lung 13 | 204 | 0.5 |
| LngSQ44 | Squamous cell carcinoma | Lung 14 | 8.70 | 61.20 |
| LngBR94 | Squamous cell carcinoma | Lung 15 | 85.0 | 0.0 |
| Lng90X | Squamous cell carcinoma | Lung 16 | 12.7 | 7.3 |
| LngLC71 | Large cell carcinoma | Lung 17 | 82.14 | 71.26 |
| LngLC109 | Large cell carcinoma | Lung 18 | 94.35 | 348.50 |
| Lng75XC | Metastatic from bone cancer | Lung 19 | 1 | 3 |
| LngMT67 | Metastatic from renal cell cancer | Lung 20 | 590.18 | 20.04 |
| LngMT71 | Metastatic from melanoma | Lung 21 | 32.90 | 18.06 |
| Bld32XK | | Bladder 1 | 17.5 | 4.6 |
| Bld46XK | | Bladder 2 | 3.4 | 5.8 |
| ClnAS67 | | Colon 1 | 28.4 | 0.1 |
| ClnC9XR | | Colon 2 | 29 | 10 |
| ClnTX67 | | Colon 3 | 78 | 2 |
| End28XA | | Endometrium 1 | 49.2 | 35.4 |
| End12XA | | Endometrium 2 | 13 | 13 |
| Kid106XD | | Kidney 1 | 16.6 | 52.2 |
| Kid107XD | | Kidney 2 | 1992.0 | 61.0 |
| Kid109XD | | Kidney 3 | 641 | 53 |
| Liv94XA | | Liver 1 | 30.0 | 1.6 |
| Liv15XA | | Liver 2 | 5 | 3 |
| MamA06X | | Liver 3 | 20.9 | 1.1 |
| MamB011X | | Mammary gland 1 | 46.7 | 0.2 |
| Mam12X | | Mammary gland 2 | 80 | 97 |
| Ovr103X | | Ovary 1 | 44.2 | 0.9 |
| Ovr1005O | | Ovary 2 | 40 | |
| Ovr1028 | | Ovary 3 | 136 | |
| Ovr18GA | | Ovary 4 | | 116 |
| Ovr206I | | Ovary 5 | | 5 |
| Pan71XL | | Pancreas 1 | 0.5 | 0.4 |
| Pan77X | | Pancreas 2 | 21 | 7 |
| Pro20XB | | Prostate 1 | 2.9 | 15.9 |
| Pro12B | | Prostate 2 | 11 | 2 |
| Pro13XB | | Prostate 3 | 0.6 | 10 |
| SmIH89 | | Small Intestine 1 | 28 | 6 |
| StoAC44 | | Stomach 1 | 8 | 24 |
| Tst39X | | Testis 1 | 184.8 | 1.8 |
| Utr135XO | | Uterus 1 | 88.0 | 138.6 |
| Utr141XO | | Uterus 2 | 110 | 65 |
| Utr23XU | | Uterus 3 | 58 | 41 |

0=Negative

In the analysis of matching samples, the higher levels of expression were in lung tissue. In addition to the expression in lung, Lng108 was also expressed in all other 14 tissue types tested. These results confirmed that Lng108 is expressed higher in lung but also is expressed in other tissue types analyzed and is consistent with the results obtained with the panel of normal pooled samples (Table 1).

Furthermore, the level of mRNA expression was compared in cancer samples and the isogenic normal adjacent tissue from the same individual. This comparison provides an indication of specificity for the cancer stage (e.g. higher levels of mRNA expression in the cancer sample compared to the normal adjacent). Table 2 shows overexpression of Lng108 in 14 out of 21 (67%) lung cancer tissues compared with their respective normal adjacent. Overexpression of Lng108 was also found in other cancer samples compared to the normal adjacent tissues (bladder, colon, endometrium, kidney, liver, mammary, ovary, prostate, small intestine, testis and uterus). Overall, these results show overexpression of Lng108 in 36 out of 48 (75%) cancer tissues tested compared to the normal adjacent.

Thus, the mRNA expression in many different tissue types, plus the observed overexpression in 75% of all the cancer matching samples tested is indicative of Lng108 being a lung cancer diagnostic marker and a general cancer diagnostic marker.

What is claimed is:

1. A method of identifying molecules for use in imaging cancer comprising screening molecules for an ability to bind to Lng108 wherein the ability of a molecule to bind to Lng108 is indicative of the molecule being useful in imaging cancer.

2. The method of claim 1 wherein the cancer is lung cancer.

3. The method of claim 1 wherein the molecule is an antibody.

4. The method of claim 3 wherein the antibody is a monoclonal antibody.

5. A method of imaging or treating cancer in a patient comprising administering to the patient an antibody which specifically binds to Lng108.

6. The method of claim 5 wherein said antibody is labeled with paramagnetic ions or a radioisotope.

7. The method of claim 5 wherein the antibody is conjugated to a cytotoxic agent.

8. The method of claim 5 wherein the cancer is lung cancer.

9. The method of claim 5 wherein the antibody is a monoclonal antibody.

10. A method of treating cancer in a patient comprising administering to the patient an antibody which downregulates expression or activity of Lng108.

11. The method of claim 10 wherein the cancer is lung cancer.

12. The method of claim 10 wherein the antibody is a monoclonal antibody.

13. A method of identifying molecules for use in treating cancer comprising screening molecules for an ability to bind to or decrease expression of Lng108 wherein the ability of a molecule to bind to or decrease expression of Lng108 is indicative of the molecule being useful in treating cancer.

14. The method of claim 13 wherein the cancer is lung cancer.

15. The method of claim 13 wherein the molecule is an antibody.

16. The method of claim 15 wherein the antibody is a monoclonal antibody.

17. The method of claim 15 wherein the antibody is conjugated to a cytotoxic agent.

* * * * *